United States Patent [19]

Turnbull

[11] Patent Number: 5,324,741
[45] Date of Patent: Jun. 28, 1994

[54] HETEROCYCLIC ISOXAZOLE COMPOUNDS HAVING NEMATICIDAL ACTIVITY

[75] Inventor: Michael D. Turnbull, Earley, United Kingdom

[73] Assignee: Imperial Chemical Industries plc, Millbank, United Kingdom

[21] Appl. No.: 610,607

[22] Filed: Nov. 8, 1990

[30] Foreign Application Priority Data

Nov. 14, 1989 [GB] United Kingdom ............... 8925741

[51] Int. Cl.$^5$ .................. A01N 43/56; C07D 261/08
[52] U.S. Cl. ..................................... 514/403; 548/247
[58] Field of Search ................... 548/247; 514/403

[56] References Cited

U.S. PATENT DOCUMENTS 3,781,438  12/1973  Gibbons ........................ 424/272
3,879,532   4/1975  Hass et al. .................... 424/272
3,879,533   4/1975  Carr et al. .................... 424/272

OTHER PUBLICATIONS

Chemical Abstracts 79012y Nematocidal chloromethyl-isoxazoles. Mayer et al., 1969.
Chemical Abstracts, vol. 72, No. 25, Apr. 13, 1970, Mayer et al. "Nematocidal chloromethylisoxazoles", p. 402, abstract No. 79012y.
Chemical Abstracts, vol. 107, No. 21, Nov. 23, 1987, Mizukai et al., "Preparation of 3-hydroxy-4-mercaptoisoxazoles . . . " p. 763, abstract No. 298 301t.
Chemical Abstracts, vol. 111, No. 17, Oct. 23, 1989, Linderman et al., "An efficient method for the synthesis of trifluoromethyl . . . ", p. 712, abstract No. 153 697t.

Primary Examiner—Mary C. Lee
Assistant Examiner—Joseph K. McKane
Attorney, Agent, or Firm—William E. Dickheiser

[57] ABSTRACT

The compounds of formula (I):

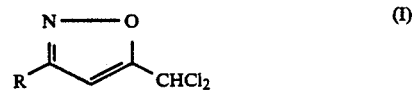

wherein R is $(CH_3)_2CHCH_2-$ or $(CH_3)_3CCH_2-$, or R is the group $CH_3-O-(R^1)CH-$ where $R^1$ is hydrogen or methyl, or R is a cycloalkyl group containing from 3 to 6 carbon atoms have nematicidal activity and the present invention discloses a method for killing or controlling nematode pests which comprises applying to the locus of the pests or to a plant susceptible to attack by the pest an effective amount of a compound of formula (I).

15 Claims, No Drawings

HETEROCYCLIC ISOXAZOLE COMPOUNDS HAVING NEMATICIDAL ACTIVITY

The present invention relates to novel isoxazole derivatives having nematicidal activity, to processes for their preparation and to compositions containing them.

South African Patent No. 6808152 describes certain chloromethylisoxazoles having nematicidal properties.

The applicants have found that certain compounds falling within the scope of this application show unexpectedly good nematicidal properties as compared with those compounds exemplified in South African Patent No. 6808152. In addition the compounds show advantageous volatility to enable them to be employed practically.

According to the present invention there is provided a compound of formula (I):

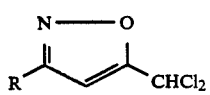
(I)

wherein R is $(CH_3)_2CHCH_2-$ or $(CH_3)_3CCH_2-$; or R is the group $CH_3-O-(R^1)CH-$ where $R^1$ is hydrogen or methyl; or R is a cycloalkyl group containing from 3 to 6 carbon atoms. When R is a cycloalkyl group it is preferably cyclopropyl or cyclopentyl.

Examples of the compounds of formula (I) are set out in Table I.

TABLE 1

| COMPOUND NO. | R | CHARACTERISING DATA |
|---|---|---|
| 1 | $(CH_3)_2CHCH_2-$ | NMR: 0.97, (d, 6H); 1.99(m, 1H); 2.57(d, 2H); 6.37(s, 1H); 6.72(s, 1H) |
| 2 | cyclopropyl | NMR: 1.0(m, 4H), 2.0(m, 1H; 6.2(s, 1H); 6.65(s, 1H) |
| 3 | cyclopentyl | Melting Point: 30° C. |
| 4 | $CH_3-O-CH_2-$ | NMR: 3.4(s, 3H); 4.5(s, 2H); 6.6(s, 1H); 6.8(s, 1H) |
| 5 | $CH_3-O-(CH_3)CH-$ | NMR: 3.3(s, 3H); 4.52(q, 1H); 5.5(d, 3H); 6.58(s, 1H); 6.73(s, 1H) |

NMR = $^1$H NMR δ ($CDCl_3$)

The compounds where R is $(CH_3)_2CHCH_2-$, $(CH_3)_3CCH_2-$ or cycloalkyl are prepared by dehydrating a compound of formula (II):

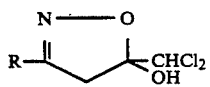
(II)

where R has the meaning stated above. The dehydration can be carried out under conventional conditions, for example, using a dehydrating agent such as concentrated hydrochloric acid, trifluoroacetic acid or thionyl chloride. The dehydration is suitably carried out using excess dehydrating agent as solvent or in an inert organic solvent such as ethanol at elevated temperatures of from 40° C. to 75° C.

The compounds of formula (II) are suitably prepared by reacting a compound of formula (III):

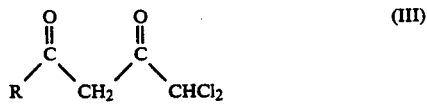
(III)

with hydroxylamine or a salt thereof in the presence of acid. The reaction is suitably carried out in an organic solvent such as lower alcohols, for example, ethanol. The reaction is carried out preferably at temperatures of from 10° C. to 30° C.

The hydroxylamine is preferably in the form of an acid addition salt such as the hydrochloride salt which ensures that protons are present.

The compounds of formula (III) are suitably prepared by reacting a compound of formula (IV):

(IV)

with a compound of formula (V):

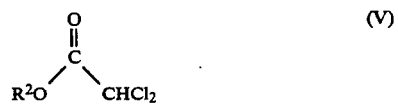
(V)

wherein $R^2$ is a $C_{1-6}$ alkyl group, for example, methyl in the presence of a strong base.

Suitable strong bases for use in the reaction include sodium ($C_{1-6}$) alkoxides such as sodium methoxide.

The reaction may be carried out in an inert organic solvent such as diethyl ether.

Compounds of formula (IV) and (V) are known compounds.

The compounds of formula (I) wherein R is the group $CH_3-O-(R^1)CH-$ and $R^1$ is hydrogen or methyl may be prepared from 3-acetyl 5-dichloromethyl isoxazole. When $R^1$ is methyl, a suitable procedure is first to reduce the acetyl group under conventional conditions, for example with sodium borohydride in a solvent such as a lower alcohol, for example, methanol. The secondary alcohol so produced is then methylated using a methylating agent, for example, methyl iodide or dimethyl sulphate in an inert organic solvent such as an ether, for example diethyl ether. If the methylating agent is a methyl halide, a catalyst such as a silver salt may be used.

When $R^1$ is hydrogen, a suitable procedure is first to convert the 3-acetyl 5-dichloromethyl isoxazole to 3-hydroxymethyl 5-dichloromethyl isoxazole using conventional methods. For example, the acetyl group may be oxidised to a carboxylate group with a high-valency metal compound, for example potassium dichromate or potassium permanganate and the acid group converted to a lower alkyl ester with a lower alcohol, for example, ethanol using an acid catalyst, for example concentrated sulphuric acid or hydrochloric acid. Reduction of the ester with a suitable reducing agent, for example sodium borohydride, in a solvent such as a lower alcohol such as ethanol completes the preparation of the hydroxy compound. This primary alcohol is then methylated using a methylating agent such as methyl iodide or dimethyl sulphate in an inert organic solvent such as an ether, for example diethyl ether. If the methylating agent is a methyl halide, a catalyst such as a silver salt may be used.

The compounds of Table I are nematicidal and can be used to control nematodes in crop plants. Therefore in a further aspect of the invention, there is provided a method for killing or controlling nematodes which comprises applying to the locus of the nematode an effective amount of a compound of formula (I).

In order to apply the compound to the locus of the nematode, the compound is usually formulated into a composition which includes in addition to the compound of formula (I) suitable inert diluent or carrier materials, and/or surface active agents.

These compositions form a further aspect of the invention.

The compositions may also comprise another pesticidal material, for example insecticide or acaricide, or a fungicide, or may also comprise an pesticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.001% and 1.0% by weight of the active ingredient (approximately equivalent to from 50–20000 g/ha) is particularly useful.

In use the compositions are applied to the nematodes, to the locus of the nematodes, to the habitat of the nematodes, or to growing plants liable to infestation by the nematodes, by any of the known means of applying pesticidal compositions, for example, by dusting, spraying or incorporation of granules.

The compounds of the invention may be the sole active ingredient of the composition or they may be admixed with one or more additional active ingredients such as nematicides, insecticides, synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

a) Pyrethroids such as permethrin, esfenvalerate, deltamethrin, cyhalothrin in particular lambda -cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazionon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;
d) Benzoyl ureas such as triflumuron, or chlorofluazuron;
e) Organic tin compounds such as cyhexatin, fenbutatin oxide, azocyclotin;
f) Macrolides such as avermectins or milbemycins, for example such as abamectin, avermectin, and milbemycin;
g) Hormones and pheromones;
h) Organochlorine compounds such as benzene hexachloride, DDT, chlordane or dieldrin;
i) Amidines, such as chlordimeform or amitraz;
j) Fumigant agents.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo- larvicides such as chlofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable synergists for use in the compositions include piperonyl butoxide, sesamax, and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S. The ratio of the compound of the invention to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

The following Examples illustrate the invention. The compounds were identified and characterised by means of the melting points, nuclear magnetic resonance spectroscopy (NMR), or infra red spectroscopy.

EXAMPLE 1

This example illustrates the preparation of Compound No. 1 of Table 1

Step a

Preparation of the compound of formula (III) wherein R is $(CH_3)_2CHCH_2-$

A mixture of methyl isobutylketone (10 g) and ethyl dichloroacetate (15.7 g) was added dropwise, to a freshly prepared solution of sodium methoxide (5.94 g) in dry diethyl ether at room temperature. During the addition, the reaction mixture became bright yellow in colour changing to orange as the reaction progressed. On completion of the addition, stirring was continued until complete conversion of starting materials was indicated by GC analysis. The reaction mixture was then acidified with 1N Hydrochloric acid (200 ml) and extracted with diethyl ether. The combined extracts were washed with water, dried over anhydrous $MgSO_4$, filtered and evaporated under reduced pressure to give an orange oil.

Yield: 17.4 g (82%).

Infra red: 1750 cm$^{-1}$, 1711 cm$^{-1}$ and 1595 cm$^{-1}$.

Step b

Preparation of the compound of formula (II) wherein R is $(CH_3)_2CHCH_2-$.

The product from Step (a) (5 g) was dissolved in ethanol (25 ml) and to the resultant stirred solution was added on aqueous solution of hydroxylamine hydrochloride (1.64 g) in a minimum amount of water. The reaction mixture was brought to reflux for one hour. The reaction mixture was allowed to cool before being quenched into a sodium bicarbonate solution and the product mixture was then extracted with diethyl ether. The combined ether extracts were dried over anhydrous $MgSO_4$, filtered and evaporated under reduced pressure to give a brown oil. The oil was triturated with 40–60 petrol ether and the desired product crystallised out, and was collected as fine creamy crystals.

Yield: 3.13 g (71%).

$^1H$ NMR (ppm): 1.0, (d, 6H); 1.9, (m, 1H); 2.25 (d, 2H); 3.1 (d, 1H); 3.3 (d, 1H); 3.7 (s, 1H); 3.89 (s, 1H).

Step c

The product from Step (b) (3.13 g) was warmed under gentle reflux in ethanol (30 ml) and concentrated hydrochloric acid (15 ml). After 3.5 hours the reaction mixture was allowed to cool and then quenched by pouring into water. The product was extracted into ether and the combined ether extracts washed with sodium bicarbonate solution before drying over anhydrous magnesium sulphate. The extracts were filtered and evaporated under reduced pressure to give an orange/brown oil.

The oil was distilled under reduced pressure to give Compound No. 1 of Table 1 as a colourless oil.

Yield: 1.62 g (56%).

Boiling point: 75°–80° C. (0.02 m bar).

NMR taken 1H: 0.97, (d, 6H); 1.99 (m, 1H); 2.57 (d, 2H); 6.37 (s, 1H); 6.72 (s, 1H).

$^{13}C$ NMR (ppm): 167.4, 163.3, 103.8, 60.1, 35.0, 27.9, 22.3.

Compound Nos. 2 and 3 of Table 1 are prepared by analogy using the preparative route of Example 1.

EXAMPLE 2

This example illustrates the preparation of compound no. 4 of Table 1.

Step a

Preparation of

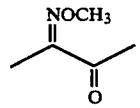

2,3-Butanedione monoxime (100 g) in 250 ml of acetone was added to a stirred suspension of potassium carbonate (136 g) in 600 ml of acetone. During the addition the suspension became yellow in colour and after the addition the suspension was stirred for one hour. Dimethyl sulphate (124 g) was then added dropwise at a rate such that the resultant exotherm did not exceed 35° C. A creamy white suspension resulted which was stirred for 2 hours and then warmed to gently reflux for a further 2 hours. The reaction mixture was allowed to cool before filtering. The excess acetone was distilled out using a fractionating column leaving a pale brown oil. This oil was distilled under partial vacuum to give a pale yellow oil.

Yield = 94 g (82%)
Boiling Point: 58°-60° C. at 93 mm Hg
¹H NMR δ(CDCl₃): 1.9 (s, 3H); 2.35 (s, 3H); 4.1 (s, 3H)

Step b

Preparation of

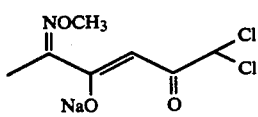

The product from step a (94 g) and methyldichloroacetate (117 g) were added as a mixture to a stirred suspension of sodium methoxide (49 g) in 750 ml of dry diethylether. Exotherm was controlled with an ice/water bath. During the addition a brown solution resulted and after the addition this changed to a yellow precipitate. The precipitate was filtered and washed with ether (250 ml) and the filter cake was allowed to air dry.

Yield = 114.2 g (59%)

Step c

Preparation of

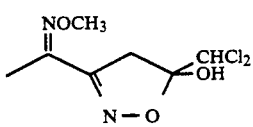

The product from step b (114.2 g) was dissolved in ethanol (1200 ml) and a solution of hydroxylamine hydrochloride (32 g in 100 ml) was added dropwise over 1 hour. After the addition the reaction mixture was left to stir overnight. The reaction was then filtered and the filtrate was evaporated under reduced pressure to give a yellow solid. This solid was recrystallised from hexane to give yellow crystals.

Yield = 73 g (66%)
¹H NMR δ(CDCl₃): 2.1 (s, 3H); 3.4 (q, 2H); 3.6 (s, 1H); 4.0 (s, 3H); 5.9 (s, 1H)

Step d

Preparation of

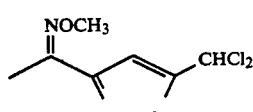

The product from step c (71 g) was dissolved in thionyl chloride (100 ml) and the reaction mixture was heated to gentle reflux for 2 hours. The reaction was allowed to cool before removing the excess thionyl chloride under reduced pressure. The remaining orange oil was distilled under high vacuum to yield a pale yellow oil (boiling point: 58°-68° C. at 0.05 mmHg). The oil was crystallised from 40/60 petrol ether at low temperature to give colourless needles.

Yield = 47 g (72%)
¹H NMR δ(CDCl₃): 2.25 (s, 3H); 4.0 (s, 3H); 6.7 (s, 1H); 6.9 (s, 1H)

Step e

Preparation of

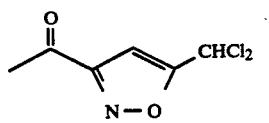

The product from step d (37 g) was added to a mixture of levulinic acid (50 ml) and concentrated hydrochloric acid (50 ml) and the reaction mixture was warmed to 90° C. for 6 hours. The reaction was allowed to cool and was then poured onto solid sodium bicarbonate. Once the carbon dioxide had been evolved, the resultant slurry was diluted with water (200 ml) and then filtered. The filtrate was extracted with diethyl ether (3 times) and the combined organic extracts were dried over anhydrous magnesium sulphate, filtered and evaporated under reduced pressure to yield a brown oil. The oil was distilled in a kugelrohr distillation apparatus to give a colourless oil (boiling point: 60°-62° C. at 0.05 mmHg).

Yield = 22 g (69%)
¹H NMR δ(CDCl₃): 2.7 (s, 3H); 6.8 (s, 1H); 6.9 (s, 1H)

Step f

Preparation of

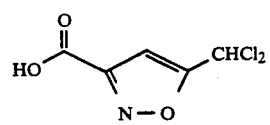

The product from step e (10 g) was added in one portion to a stirred solution of potassium dichromate (44 g) in 300 ml of 2N sulphuric acid. The mixture was warmed to 80° C. for 6 hours. During this time the colour changed from orange to green. The resultant green solution was cooled and then extracted several times with ethyl acetate. The combined organic extracts were washed several times with sodium bicarbonate and then discarded. The combined aqueous extracts were re-acidified with 2N hydrochloric acid and then extracted several times with ethyl acetate. The combined organic extracts were dried over anhydrous magnesium sulphate, filtered and the solvent removed under reduced pressure to give a pale green solid.

Yield = 7.68 g (76%)

Step g

Preparation of

The product from step f (3.6 g) was added to a stirred mixture of ethanol (35 ml) containing 0.1 ml of concentrated sulphuric acid and then warmed to reflux for 3 hours. The excess ethanol was removed under reduced pressure to give a yellow solid. This solid was chromatographed through silica eluting with Hexane/diethyl ether (5:1) to yield a white crystalline solid.

Yield = 2.7 g (66%)
Melting point = 81°-82° C.
$^1$H NMR δ(CDCl$_3$): 1.4 (t, 3H); 4.4 (q, 2H), 6.8 (s, 1H); 6.98 (s, 1H)

Step h

Preparation of

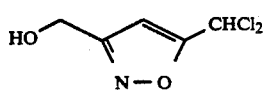

The product from step g (2.5 g) was dissolved in 50 ml of ethanol and (0.45 g) of sodium borohydride was added portionwise over 10 minutes at 0° C. After the addition the mixture was left to stir for 1 hour at 0° C. before allowing to warm to room temperature.

The reaction mixture was then evaporated to leave a white slurry which was diluted with water (20 ml) and extracted into diethylether. The combined organic extracts were dried over anhydrous magnesium sulphate, filtered and the solvent removed to give a colourless oil.

Yield = 2 g (99%)
$^1$H NMR δ(CDCl$_3$): 2.5 (s, 1H); 5.75 (d, 2H); 6.6 (s, 1H), 6.75 (s, 1H)
Infra Red C=N @ 1604 cm$^{-1}$,

Step i

Preparation of Compound 4 of Table 1.

The product from step h (0.5 g) was dissolved in diethyl ether (10 ml) and methyl iodide (0.78 g) was added in one portion. Silver II oxide (0.5 g) was added to the reaction mixture with stirring and the reaction mixture was left to stir for 4 hours. The insoluble silver salts were filtered and the filtrate was evaporated down to leave a pale yellow oil.

Yield = 0.5 g (94%)
$^1$H NMR δ(CDCl$_3$): 3.4 (s, 3H); 4.5 (s, 2H); 6.6 (s, 1H); 6.8 (s, 1H)

EXAMPLE 3

This example illustrates the preparation of compound no. 5 of Table 1.

Step a

Preparation of

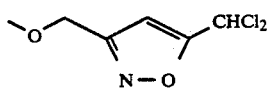

The product from Step e of Example 2 (2 g) was dissolved in 40 ml of methanol and 0.38 g of sodium borohydride was added in portions over 10 minutes at 0° C. After the addition the mixture was left to stir for 1 hour at 0° C. before allowing the temperature to rise to room temperature. The reaction mixture was evaporated which left a white slurry. This was diluted with water and extracted into diethyl ether (30 ml). The organic extracts were combined and dried over anhydrous magnesium sulphate, then filtered and the solvent removed to give a colourless oil.

Yield = 2 g (99%)
$^1$H NMR δ(CDCl$_3$): 1.58 (d, 3H); 2.0 (d, 1H); 5.0 (q, 1H); 6.6 (s, 1H); 6.76 (s, 1H)

Step b

Preparation of Compound No. 5 of Table 1

The product from Step a (1.5 g) was dissolved in 50 ml of diethyl ether and 2.2 g of methyl iodide was added in a single portion. The reaction mixture was stirred and 1.8 g of silver II oxide was added. The reaction mixture was stirred for a further 2 days. The insoluble silver salts were filtered and the filtrate was evaporated to leave a pale yellow oil which was distilled under reduced pressure to give compound no. 5 of Table 1 as a colourless oil.

Yield = 850 mg (53%)
Boiling point = 96°-98° C. (at 1.0 mmHg)
$^1$H NMR δ(CDCl$_3$): 3.3 (s, 3H); 4.52 (q, 1H); 5.5 (d, 3H); 6.58 (s, 1H); 6.73 (s, 1H)

EXAMPLE 4

In order to illustrate the nematicidal properties of the compounds of formula (I), tomato plants (6-8 weeks old, variety 'Moneymaker') were planted out into soil infested with root-knot nematodes (*Meloidogyne incognita*) and the soil drenched with a composition of a compound of formula (I) (obtained by diluting 1 part of a solution of the compound in a 1:1 mixture of acetone and ethanol with 99 parts of water containing 1% of a wetting agent) at a rate of 200 ml/kg of soil. The roots of the plants were examined after 3 weeks to determine the % reduction in the number of root knots as compared with a similar treatment omitting the compound. The results are given in Table II.

Also included in Table II are the results for 3-tertiary-butyl-5-dichloromethyl-isoxazole (compound A) as a comparison with the closest prior art. This compound was disclosed in BE 726329 (Example B). The compound was prepared from 3,3-dimethyl-2-butanone by the route given in Example 1.

TABLE II

| COMPOUND NO. | APPLICATION RATE (ppm) | % ROOT KNOT REDUCTION |
|---|---|---|
| 1 | 5 | 99 |
| 1 | 2.5 | 96 |
| 2 | 5 | 98 |
| 2 | 2.5 | 89 |
| 3 | 2.5 | 84 |
| 3 | 0.6 | 33 |
| 4 | 5 | 100 |
| 4 | 1 | 85 |
| 5 | 2.5 | 95 |
| 5 | 1.25 | 64 |
| A | 25 | 95 |
| A | 10 | 75 |

The compounds of the present invention are clearly superior to the compounds of the prior art having on average 10 times greater activity. Furthermore, poor symptomology was observed with compound A which gave high levels of foliar and root phytotoxicity.

The following examples demonstrate formulations suitable for applying the compounds of the present invention. The amount of ingredient is expressed in parts by weight or grams per liter as indicated.

EXAMPLE 9

This example demonstrates granules suitable for soil application. The granules can be made be standard techniques such as impregnation, coating, extrusion or agglomeration.

| Impregnated granule: | Active ingredient | 5 |
| --- | --- | --- |
| | Wood Rosin | 2.5 |
| | Gypsum granules (20–40 mesh) | 92.5 |
| Coated granule: | Active ingredient | 5 |
| | Solvesso* 200 | 4 |
| | Calcium carbonate granules (30–60 mesh) | 91 |
| Slow release granule: | Active ingredient | 10 |
| | Polyvinylacetate/vinyl chloride copolymer latex | 5 |
| | Attapulgus granules | 85 |

EXAMPLE 10

This example demonstrates formulations for use as a spray. The compounds can be formulated as wettable powders, water dispersible granules, emulsifiable concentrates, emulsions or microcapsule suspensions for application diluted in water.

| Emuslifiable concentrate: | Active ingredient | 250 |
| --- | --- | --- |
| | Calcium dodecyl benzene sulphonate | 50 |
| | Nonyl phenol ethoxylate | 50 |
| | Alkylbenzene solvent | to 1 liter |
| Wettable powder: | Active ingredient | 45 |
| | lignosulphonate dispersant | 5 |
| | silica | 25 |
| | sodium lauryl sulphate | 20 |
| | china clay (kaolin) | 5 |
| Microcapsule suspension: | Active ingredient | 250 |
| | toluene diisocyanate | 10 |
| | polymethylene polyphenyl isocyanate | 20 |
| | nonyl phenol ethoxylate | 6 |
| | lignosulphonate dispersant | 15 |
| | xanthan gum | 1 |
| | bentonite | 10 |
| | biocide 'Proxel'* | 0.1 |
| | sodium carbonate | 5 |
| | water | to 1 liter |

The microcapsule suspensions can be used as a spray, soil drench or as an intermediate to prepare slow release granules for application to the soil

I claim:
1. A compound of formula (I):

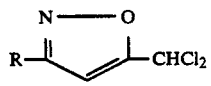

wherein R is $(CH_3)_2CHCH_2$—; or R is the group $CH_3$—O—$(R^1)CH$— where $R^1$ is hydrogen or methyl; or R is a cycloalkyl group containing from 3 to 6 carbon atoms.

2. A nematicidal composition comprising an effective amount of a compound of formula (I):

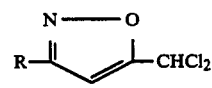

wherein R is $(CH_3)_2CHCH_2$—; or R is the group $CH_3$—O—$(R^1)CH$— where $R^1$ is hydrogen or methyl; or R is a cycloalkyl group containing from 3 to 6 carbon atoms.

3. A method for killing or controlling nematode pests which comprises applying to the locus of the pests or to a plant susceptible to attack by the pest an effective amount of a compound of formula (I) as defined in claim 1.

4. Compounds of formula

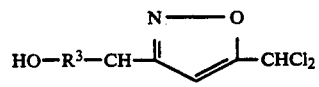

wherein $R^3$ is hydrogen or methyl.

5. A compound according to claim 1 wherein R is $(CH_3)_2CHCH_2$.

6. A compound of formula

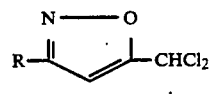

wherein R is $CH_3$—O—$R^1CH$— wherein $R^1$ is hydrogen or methyl or R is a cycloalkyl group containing from 3 to 6 carbon atoms.

7. A compound according to claim 6 wherein R is $CH_3$—O—$CH_2$.

8. A compound according to claim 6 wherein R is $CH_3$—O—$(CH_3)CH$—.

9. A compound according to claim 6 wherein R is cyclopropyl.

10. A compound according to claim 6 wherein R is cyclopentyl.

11. A composition according to claim 2 wherein R is $(CH_3)_2CHCH_2$.

12. A composition according to claim 2 wherein R is $CH_3$—O—$CH_2$—.

13. A composition according to claim 2 wherein R is $CH_3$—O—$(CH_3)CH$—.

14. A composition according to claim 2 wherein R is cyclopropyl.

15. A composition according to claim 2 wherein R is cyclopentyl.

* * * * *